(12) United States Patent
Hamada et al.

(10) Patent No.: US 8,388,669 B2
(45) Date of Patent: Mar. 5, 2013

(54) HAIR GROWTH MODULATING METHOD AND MODULATION DEVICE THEREOF

(75) Inventors: Chosei Hamada, Kadoma (JP); Masato Kinoshita, Kadoma (JP); Takashi Matsuzaki, Matsue (JP); Toshitatsu Nogita, Nerima-ku (JP)

(73) Assignees: Panasonic Corporation, Osaka (JP); National University Corporation Shimane University, Shimane (JP)

( * ) Notice: Subject to any disclaimer, the term of this patent is extended or adjusted under 35 U.S.C. 154(b) by 720 days.

(21) Appl. No.: 12/593,604

(22) PCT Filed: Dec. 25, 2007

(86) PCT No.: PCT/JP2007/074860
§ 371 (c)(1),
(2), (4) Date: Sep. 28, 2009

(87) PCT Pub. No.: WO2008/129740
PCT Pub. Date: Oct. 30, 2008

(65) Prior Publication Data
US 2010/0131035 A1    May 27, 2010

(30) Foreign Application Priority Data

Mar. 30, 2007  (JP) .................. 2007-094806

(51) Int. Cl.
*A61N 5/06* (2006.01)
*A61B 19/00* (2006.01)
*A61B 18/18* (2006.01)

(52) U.S. Cl. ............... 607/88; 128/898; 606/9

(58) Field of Classification Search .............. 607/88–93; 128/898; 606/9
See application file for complete search history.

(56) References Cited

U.S. PATENT DOCUMENTS

| | | |
|---|---|---|
| 5,713,961 A | 2/1998 | Caisey et al. |
| 6,168,590 B1 | 1/2001 | Neev |
| 6,902,563 B2 | 6/2005 | Wilkens et al. |
| 2002/0161418 A1 | 10/2002 | Wilkens et al. |
| 2002/0169442 A1 | 11/2002 | Neev |
| 2002/0173781 A1* | 11/2002 | Cense et al. ............. 606/9 |
| 2003/0004499 A1 | 1/2003 | McDaniel |
| 2003/0023283 A1 | 1/2003 | McDaniel |
| 2004/0034319 A1 | 2/2004 | Anderson et al. |

(Continued)

FOREIGN PATENT DOCUMENTS

| | | |
|---|---|---|
| JP | 58-83934 A | 5/1983 |
| JP | 60-106444 A | 6/1985 |

(Continued)

OTHER PUBLICATIONS

International Search Report for the Application No. PCT/JP2007/074860 mailed Jan. 29, 2008.

(Continued)

*Primary Examiner* — Dawayne A Pinkney
(74) *Attorney, Agent, or Firm* — Cheng Law Group, PLLC

(57) ABSTRACT

A modulating light having a wavelength of 400 nm to 600 nm is irradiated to a portion around hair roots at an energy of 0.01 J/cm² to 1 J/cm² over a time period of not more than 1 ms as a flash light such that a light absorptive component existing in a human body around the hair roots absorbs the light for modulating hair growth without causing substantial adverse effect.

10 Claims, 13 Drawing Sheets

U.S. PATENT DOCUMENTS

| | | |
|---|---|---|
| 2004/0153131 A1 | 8/2004 | Yorke |
| 2004/0230258 A1* | 11/2004 | Altshuler et al. ............. 607/88 |
| 2005/0085878 A1 | 4/2005 | Wilkens et al. |
| 2007/0073276 A1 | 3/2007 | Wilkens et al. |

FOREIGN PATENT DOCUMENTS

| | | |
|---|---|---|
| JP | 8-71166 A | 3/1996 |
| JP | 2002-541906 A | 12/2002 |
| JP | 2004-532671 A | 10/2004 |
| JP | 2005-519692 A | 7/2005 |
| JP | 2006-501960 A | 1/2006 |
| JP | 2006-515772 A | 6/2006 |
| WO | WO-99/07438 A1 | 2/1999 |
| WO | WO-00/62700 A1 | 10/2000 |
| WO | WO-00/74781 A1 | 12/2000 |
| WO | WO-03/077783 A1 | 9/2003 |
| WO | WO-2004/033040 A1 | 4/2004 |
| WO | WO-2004/064923 A1 | 8/2004 |

OTHER PUBLICATIONS

Russian Official Action for Application No. 2009140054/14(056873) from the Russian Federal Service for Intellectual Property, Patents, and Trademarks dated Feb. 14, 2011.

Supplementary European Search Report for the Application No. EP 07 86 0089 dated Oct. 8, 2012.

* cited by examiner

Fig.2
(A)
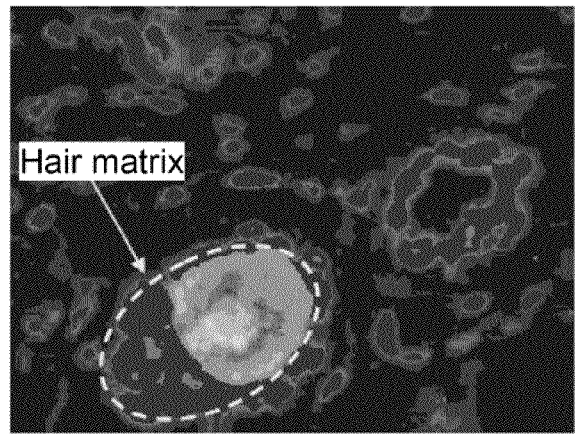
(B)
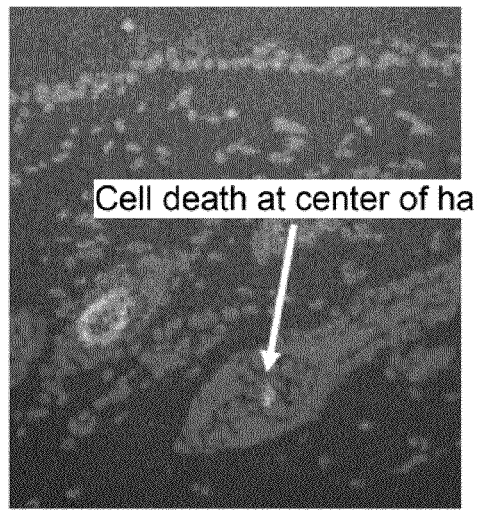
(C)
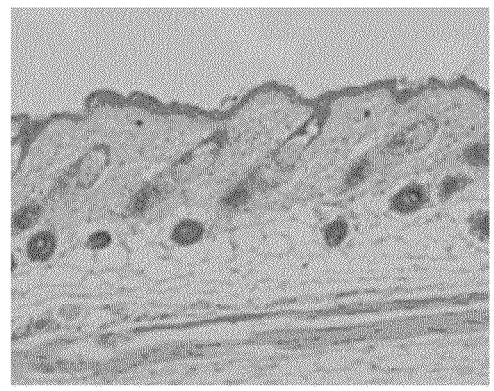

HAIR GROWTH MODULATING METHOD AND MODULATION DEVICE THEREOF

TECHNICAL FIELD

The present invention relates to a hair growth modulating method that modulates growth of hair with light, and a modulation device thereof.

BACKGROUND ART

Removal of hair by irradiating with light is known in the field of medicine. This involves the removal of hair by necrosis in which cells of hair roots (and hair follicles) are destroyed using a high output (class 4) laser. However, since side effects such as burns and age spots easily occur accompanying cell destruction, this procedure can only be performed by specialized physicians.

Although it would be desirable to enable hair removal and hair regeneration to be able to be easily performed at home, there is currently no such technology capable of responding to this demand. Furthermore, although there is an instrument for assisting hair growth and hair generation described in Japanese Patent Publication No. 2002-541906 that imparts microvibrations to the scalp while irradiating with light, the irradiation of light in this case is for assisting penetration of a hair tonic into the scalp that supplies nutrients to hair papilla, and the irradiation of light is not intended to act on hair growth or hair regeneration. Although Japanese Patent Publication No. 2005-519692 proposes a method for inhibiting hair growth with low-power light, adequate effects are unable to be obtained with only the technology indicated therein.

DISCLOSURE OF THE INVENTION

With the foregoing in view, an object of the present invention is to provide a hair growth modulating method capable of modulating hair growth by irradiating low output light without causing substantial adverse effects, and a modulation device thereof.

The hair growth modulating method as claimed in the present invention is characterized in that hair growth is modulated by irradiating modulating light having a wavelength of 400 nm to 600 nm and energy of 0.01 J/cm$^2$ to 1 J/cm$^2$ to a portion around hair roots of a human body such that the modulating light is absorbed by a light absorptive component of the human body existing around the hair roots.

When absorbed by components in the body containing melanin in the vicinity of hair roots, this modulating light causes the following phenomena:
1) interruption of cell growth and induction of cell death by causing the formation of active oxygen and other radicals resulting in denaturation of DNA, proteins, cell membranes and the like;
2) induction of cell death due to the formation of stress response proteins attributable to generated heat (heat shock proteins);
3) interruption of hair growth due to mobilization or activation of transcription regulatory factors in the form of myc and p53 protein;
4) changes in the thickness and length of hair regenerated following a reduction in the number of hair matrix cells;
5) inhibition of the actions of enzymes that prevent escape of dopaquinone and dopachrome that occurs during the melanin formation process as a result of irradiating pigment cells with light, and occurrence of cell death due to escape of cytotoxic dopaquinone, dopachrome and the like;
6) hair expulsion; and,
7) transition from the growth period to the rest period in the hair cycle. Thus, instead of destroying cells in the manner of conventional therapeutic optical hair removal technology, hair growth is modulated by artificially inducing normal cell changes that occur in the body or physiological cell death that normally occurs during the regressive period of the hair cycle (apoptosis). Moreover, since components that absorb light are not supplied from outside the body, but rather components such as melanin that are inherently present in the body are made to absorb the light, there are few adverse effects attributable to thermal or chemical changes.

In addition, if the irradiated energy of the modulating light is less than 0.01 J/cm$^2$, effects resulting from light irradiation are unable to be confirmed, while if the irradiated energy exceeds 1 J/cm$^2$, there is concern over the occurrence of other effects on the body.

This modulating light is preferably selected to have a wavelength excluding a range of 900 nm to 1500 nm. Since this wavelength range corresponds to the absorption range of water, by excluding this wavelength range, absorption of optical energy into water in the body is inhibited, thereby making it possible to reduce detrimental effects on the body.

The modulating light is preferably irradiated over a time period of not more than 1 ms. Although the energy of light irradiation is the product of the irradiation power and the irradiation time, in the case the irradiation time exceeds 1 ms, adequate effects cannot be obtained due to the relationship with irradiation power.

The present invention also provides a hair growth modulation device for realizing the hair growth modulating method described above.

In addition to a light irradiator that irradiates modulating light having a wavelength distribution of 400 to 600 nm, this hair growth modulation device is preferably provided with a measurement means for measuring an absorption spectrum that the human body absorbs upon being irradiated with the modulating light, and a control means for comparing a peak value of absorption rate at the measured absorption spectrum with an absorption rate at a specific wavelength, and variably controlling a power of the modulating light and an irradiation time. According to this control means, a suitable amount of energy can be imparted to hair roots during the growth period or regressive period of the hair cycle, hair growth can be inhibited during the growth period of the hair cycle, and hair growth can be promoted during the rest period of the hair cycle.

In this case, the control means preferably at least controls the power and the irradiation time for irradiating the light beam at a constant energy.

BRIEF DESCRIPTION OF THE DRAWINGS

FIG. 1(A) is a schematic latitudinal cross-sectional view of a light irradiator used in the present invention, while FIG. 1(B) is a schematic longitudinal cross-sectional view of the same;

FIGS. 2(A), 2(B) and 2(C) are drawings showing micrographs of hair matrix cells after irradiating with light for 10 hours;

BEST MODE FOR CARRYING OUT THE INVENTION

Figure 1:
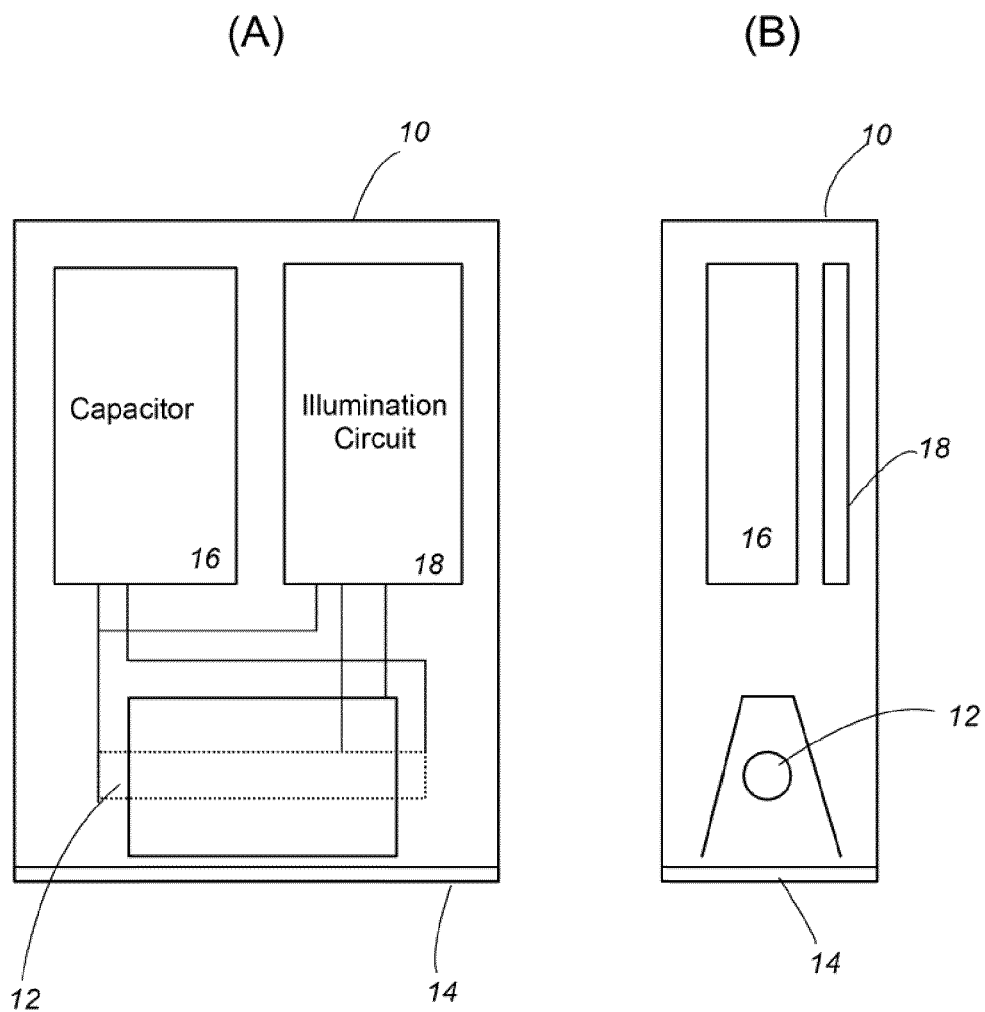

FIG. 1 shows a modulating light irradiator 10 used in the present invention. This modulating light irradiator 10 is provided with a light source in the form of a xenon flash lamp 12, and outputs modulating light in the form of flashing light having a wavelength of, for example, 400 nm to 600 nm through a filter 14. Consequently, the modulating light irradiator 10 is provided with a capacitor 14 that accumulates charge for emitting light from the xenon flash lamp 12, and a charge/discharge circuit 18 that charges and discharges the capacitor 16. The charge/discharge circuit 18 is configured to cause the xenon flash lamp 12 to emit light for a short time of no longer than 1 ms by discharging the capacitor with a one-shot pulse, and output flashing light in the form of modulating light.

Figure 12:
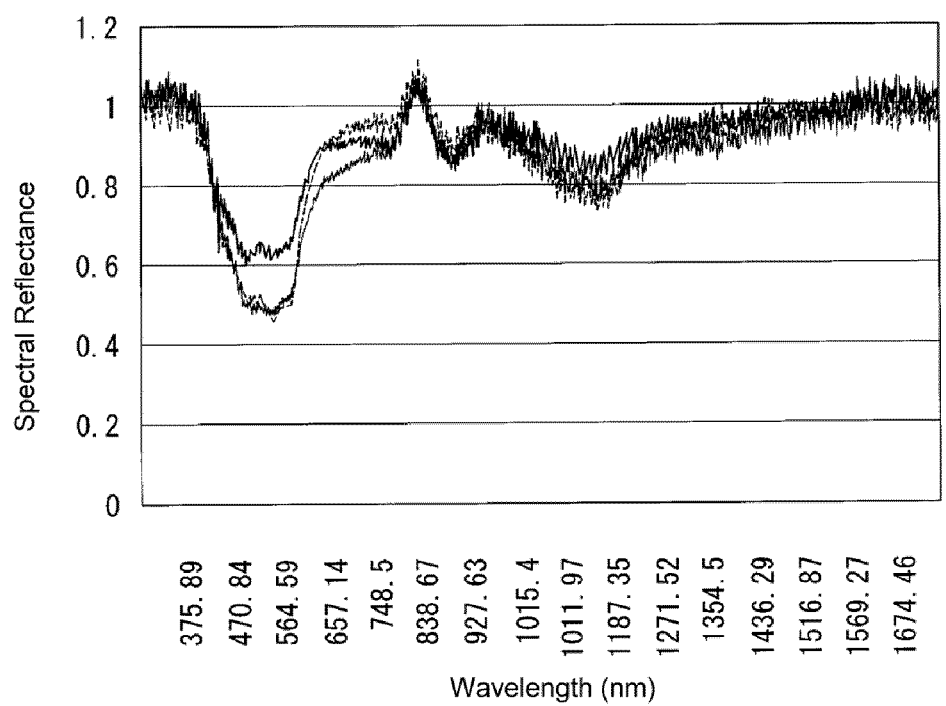
FIG. 12 is a drawing for explaining the present invention that slows the results of measuring the spectral reflectance of skin at various wavelengths of light using samples from three persons; and, FIG. 13 is a drawing for explaining the present invention that indicates the relationship between light wavelength and the absorbance of melanin alone.
Figure 13:
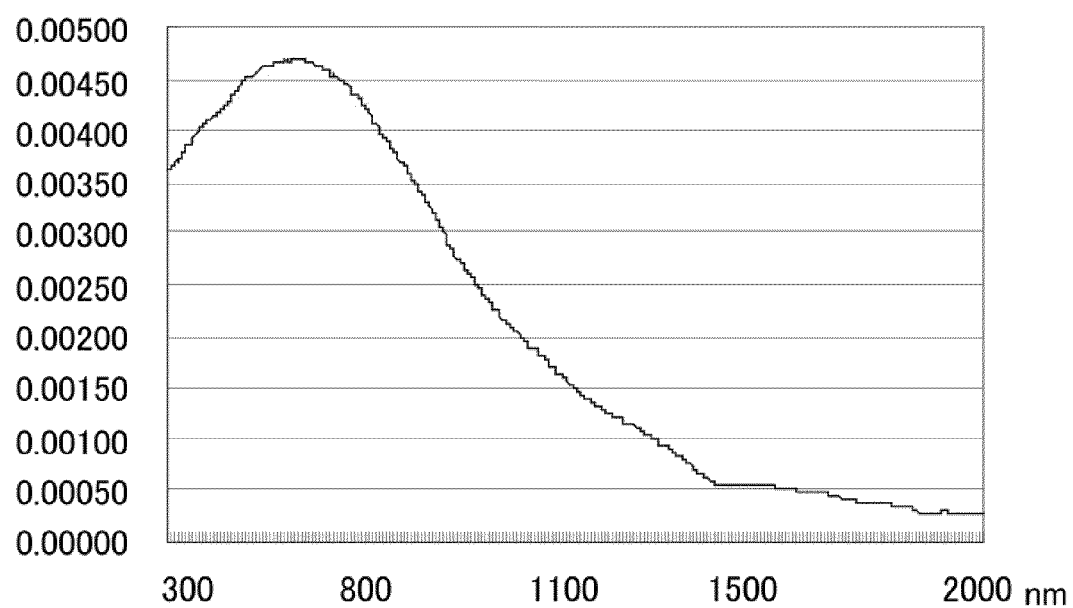

Modulating light irradiated from the modulating light irradiator 10 is required to be absorbed into the skin, and when determining the wavelength thereof, spectral reflectance of skin was measured at each light wavelength using samples from three persons as shown in FIG. 12. Reflectance in the vicinity of 400 to 600 nm decreased in all samples, and the skin was found to have properties that facilitate the absorption of light in this wavelength range. This is due to the considerable effects of melanin present in the skin. FIG. 13 shows the spectral properties of the absorbance of melanin alone, and melanin alone absorbs 39% of irradiated light in the case of a wavelength of the irradiated light of, for example, 567 nm. On the basis thereof, hair is able to be stimulated with light of a low output by using light of a wavelength band of 400 to 600 nm, which includes the wavelength of 567 nm, that is easily absorbed by skin. Furthermore, ultraviolet light having a wavelength of no more than 400 nm that is harmful to the skin is cut out with a UV cutoff filter.

Modulating light irradiated from the xenon flash lamp is irradiated at illuminance of 1,500,000 to 7,000,000 lux and a flash duration (half value of peak power) of 100 to 700 μs. Since the quantity of irradiated light can be determined as the product of illuminance and flash duration, this becomes 150 lux-seconds to 4900 lux-seconds. In addition, irradiation energy (J/cm$^2$) is the product of irradiation power (W) and irradiation time (seconds), and by controlling the irradiation power (W) and irradiation time (seconds) so that the irradiation energy K is, for example, 0.1 J/cm$^2$, the occurrence of adverse effects attributable to irradiation can be reliably suppressed. Accompanying this, when comparing the case of irradiating light once/day at intervals of several days and the case of repeatedly irradiating light once/day for 5 to 10 consecutive days, the latter allows the use of a lower power light source.

Hair (body hair and scalp hair) is known to have a hair cycle during which hair changes in cycles consisting of a growth period, a regressive period and a rest period. The inventors of the present invention confirmed in experiments using mice that if light is irradiated to the skin under the above irradiation conditions, hair growth is effectively inhibited, without causing changes in cell morphology as is observed with existing therapeutic lasers and the like and without causing destruction of cells, if the light is irradiated during the growth period of the hair cycle. Furthermore, hair growth during the growth period of the hair cycle has been confirmed to proceed rapidly if light is irradiated during the rest period of the hair cycle. In addition, adverse effects such as burns have also been confirmed to not occur.

Although the reason why hair growth is inhibited when hair is irradiated with light at a level that does not cause changes in cell morphology during the growth period is not clear, based on the results of analyses at the RNA level, activation of inflammatory cytokines is thought to occur as a result of being irradiated with light, and the resulting inhibition of hair growth is thought to be the result of this activation of inflammatory cytokines.

Furthermore, irradiation power was changed corresponding to the rate of change of spectral reflectance (or absorption rate) of the skin at an irradiated target site based on the spectral reflectance at 500 to 600 nm at which effects occurred that caused changes in the hair cycle. When the reflectance (or absorption rate) of a specific wavelength serving as a reference is defined as R0, the reflectance (or absorption rate) of the irradiated skin is defined as R1, and the power of the light source for which activation of inflammatory cytokines was achieved for the skin of R0 is defined as P0, then the irradiation power P can be determined with P=R1/R0×P0. Since the energy having an effect on the hair cycle is a constant value, in the case spectral reflectance of the skin is high, irradiation power is increased and irradiation time is shortened.

Furthermore, since the respective durations of the growth period, regressive period and rest period of the hair cycle vary according to the location such as the arms or scalp, light is irradiated after first determining whether or not the hair cycle is in the growth period for the location where hair growth is desired to be inhibited.

As has been previously described, although there are said to be effects on the inner walls of blood vessels since the wavelength region of 400 to 600 nm is the absorption wavelength of oxyhemoglobin, since the irradiation energy is low, hair growth modulation effects can be efficiently obtained at a low energy level due to absorption of light by melanin without having an effect on blood vessel inner walls.

Cell death that occurs in hair roots when irradiated with the above-mentioned light in the vicinity of the hair roots of growing hairs is depicted in FIG. 2. FIG. 2(A) depicts cells 10 hours after irradiation. At this time, a state in which a component that induces cell death (apoptosis) in the form of caspase 3 is activated appears, and the upper half of the hair matrix (side near the skin surface) is activated. In addition, confirmation of portions where cell death (apoptosis) occurs in the hair matrix revealed that cell death can be confirmed near the center of the hair matrix as shown in FIG. 2(B). However, as is clear from FIG. 2(C) depicting cell morphology 10 hours after irradiation, there are no morphological changes, thus indicating that tissue or cell destruction does not occur within the skin.

Figure 3:
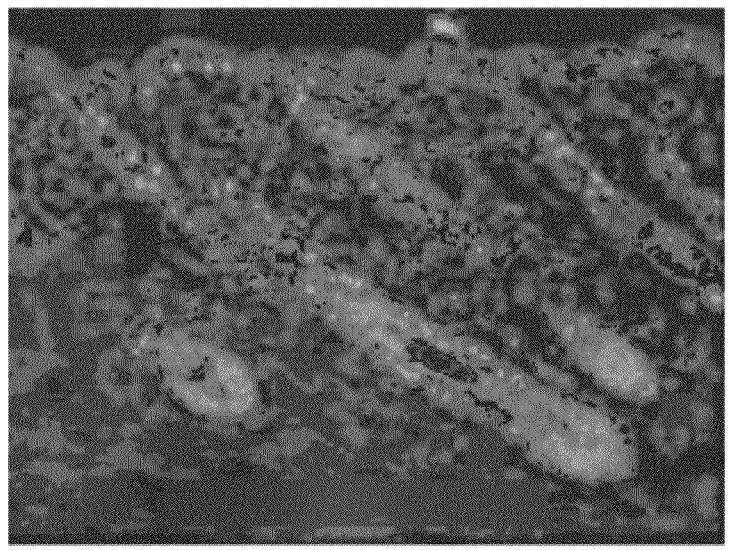
FIG. 3 is a drawing showing a micrograph of hair matrix cells after irradiating with light for 24 hours.
Figure 4:
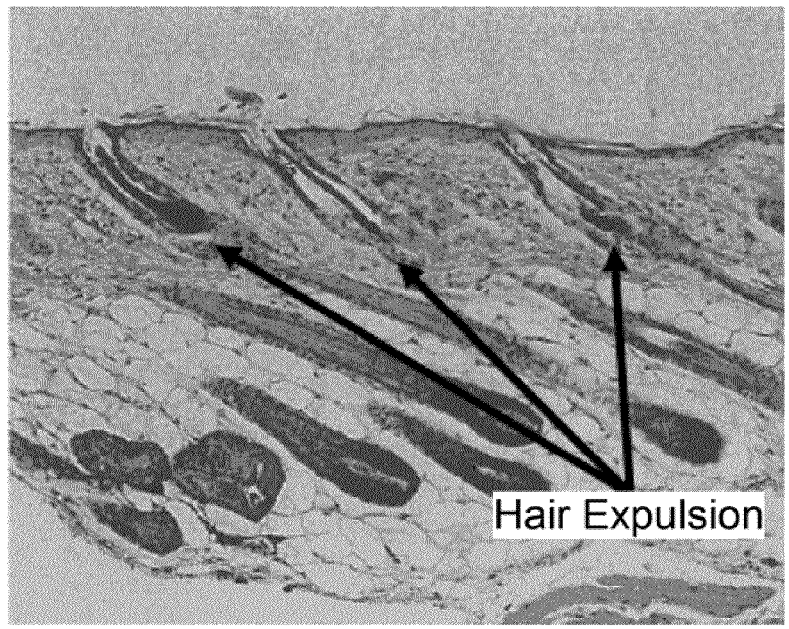
FIG. 4 is a drawing showing a micrograph of hair matrix cells in which hair expulsion has occurred after irradiating with light for 72 hours.

When cytokines were analyzed at 10 hours and 24 hours after irradiation, inflammatory cytokines were confirmed to be activated. Since growing hair roots have a function that transports melanin to the hairs and contain large amounts of melanin, irradiation of light develops hair growth modulation efficiently in hair roots. However, since light is irradiated from the upper surface of the skin, cell death only occurs in the upper half of the hair roots. Since nearly all of the light is absorbed in the upper half of the hair roots, cell death does not occur in the lower half. In addition, FIG. 3 indicates that activation of cell division occurs around hair roots 24 hours after irradiating with light (white dots indicate cells in which cell division is active), while FIG. 4 indicates that hair expulsion occurs 72 hours after irradiating with light.

The following provides an explanation of a possible reason for the occurrence of the phenomena described above. Namely, absorption of light by melanin→activation of inflammatory cytokines→change in the ratio or specific activity of p53 protein and myc protein→induction of cell death following the onset of a p53 activated state in which p53 is dominant (within about 10 hours after irradiation)→cancelation of p53 dominance and increased specific activity of myc protein→activation of cell division (about 24 hours after irradiation)→expulsion of hair roots in which cell death has occurred together with hairs (about 72 hours after irradiation).

In providing a further explanation of the above process, as a result of the reaction starting with absorption of light by melanin resulting in the occurrence of photothermal and photochemical reactions, a change occurs in the balance between p53 and myc proteins. Although inflammatory cytokines are activated prior to the occurrence of this change in balance, factors responsible for inducing this include a local temperature rise in the upper half of the hair matrix caused by a photothermal reaction of melanin in the hair matrix, and a change in the oxidation-reduction state. Thus, transcription regulation and molecular chaperone effects are thought to occur accompanying the formation or activation of a stress response protein in the form of heat shock protein.

Although p53 is a protein that induces cell death and is routinely present in cells, activation of p53 occurs as a reaction to light irradiation. Although the balance between p53 and myc is maintained in cells in the normal state, since p53 becomes dominant as a result of irradiating with light, this unbalanced state is cancelled after several hours, thereby resulting in an increase or activation of myc. Consequently, in contrast to cell death being observed 10 hours after irradiation, cell growth activity is observed after 24 hours.

In addition, light irradiation is also effective against mature pigment cells (melanocytes) present within skin as another factor that induces cell death. Although dopa, dopachrome or dihydroxyindole and the like are formed during the process by which melanin is formed in melanocytes, which are cells that form melanin, these components are cytotoxic. During the normal formation process, although enzymes function to inhibit this toxicity, when the formation process is irradiated with light and the light is absorbed by previously formed melanin, the action of the enzymes ends up being inhibited, thereby creating a situation in which the dopachrome or dihydroxyindole and the like affect cells. Cell death is induced as a result thereof.

Figure 5:
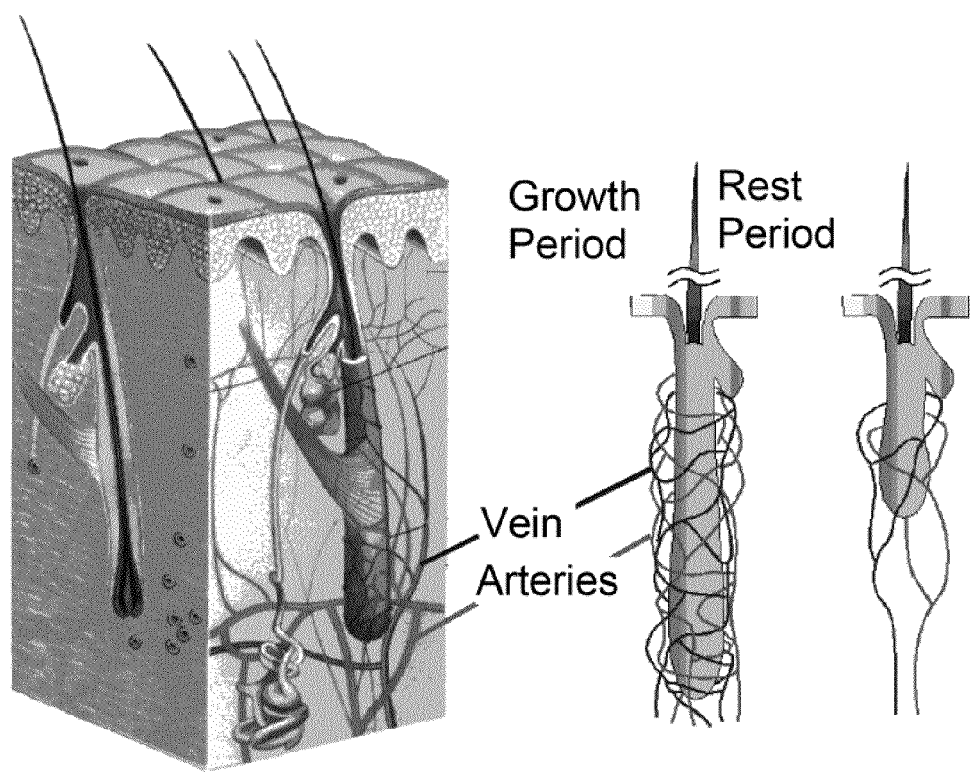
FIG. 5 is an explanatory drawing of blood vessels surrounding an organ responsible for forming hair in the form of a hair follicle.
Figure 6:
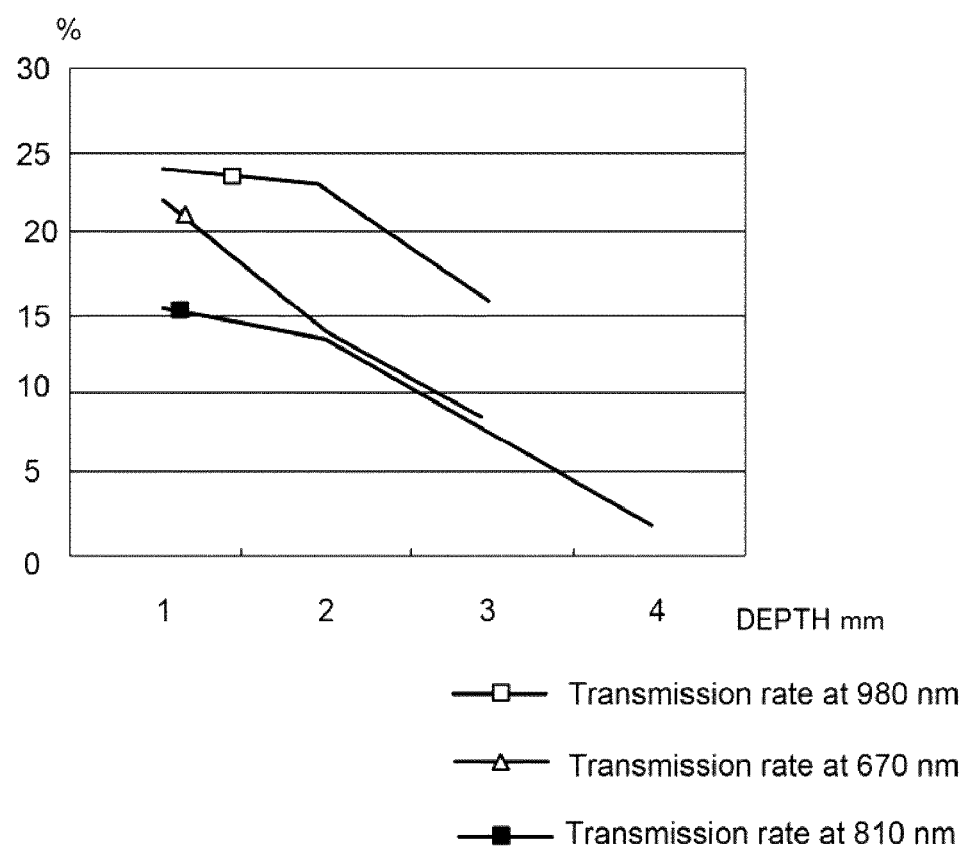
FIG. 6 is an explanatory drawing showing the transmission rates of light entering into skin.

Active oxygen is another factor that induces cell death. Hemoglobin has a structure in Fe is located in the center of a tetrapyrrole ring, and this structure is known to form active oxygen by absorbing visible light. Blood vessels are present around growing hairs (and the number of these blood vessels is greater in the growth period than in the rest period of the cell cycle to be described later: see FIG. 5, and hemoglobin, which is a constituent of the blood in these blood vessels, produces active oxygen. Accordingly, cells are damaged due to the formation of active oxygen as a result of allowing the hemoglobin in blood to absorb light. Furthermore, since the energy of the light source used is held to a low level, this effect extends to about 4 mm beneath the skin where the hair matrix is present, and does not affect deeper blood vessels. FIG. 6 shows light transmission rates in the direction of tissue depth at multiple wavelengths.

Figure 7:
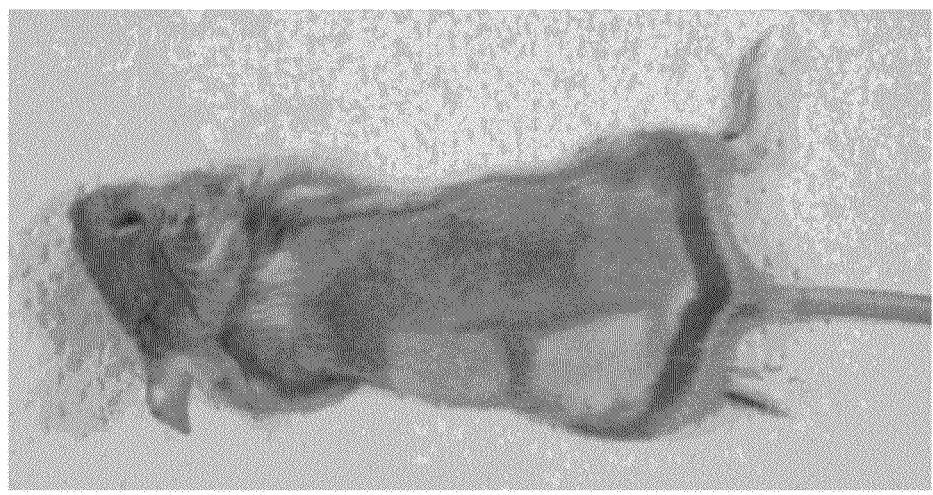
FIG. 7 is an explanatory drawing showing the results of an experiment using mice.

FIG. 7 shows the results of light irradiation in mice. The locations where hair growth has slowed are the areas irradiated with light. The effects of this light irradiation on the human body have already been confirmed. Furthermore, since hair growth (length and thickness) is defined according to the number of hair follicular germinative cells, and this number correlates with the number of hair matrix cells, in a state in which the number of hair matrix cells have decreased due to cell death, the next new hairs to be regenerated are created from a smaller number of hair follicular germinative cells. Consequently, by inducing cell death of hair matrix cells by irradiating with light and reducing the number of hair matrix cells prior to hair expulsion, the thickness of newly formed hairs can be reduced and the growth period can be shortened. Thus, by repeating hair matrix cell reduction effects, the cell cycle can be ultimately altered to a downy type of hair cycle in which hardly any hairs appear on the skin surface.

Figure 8:
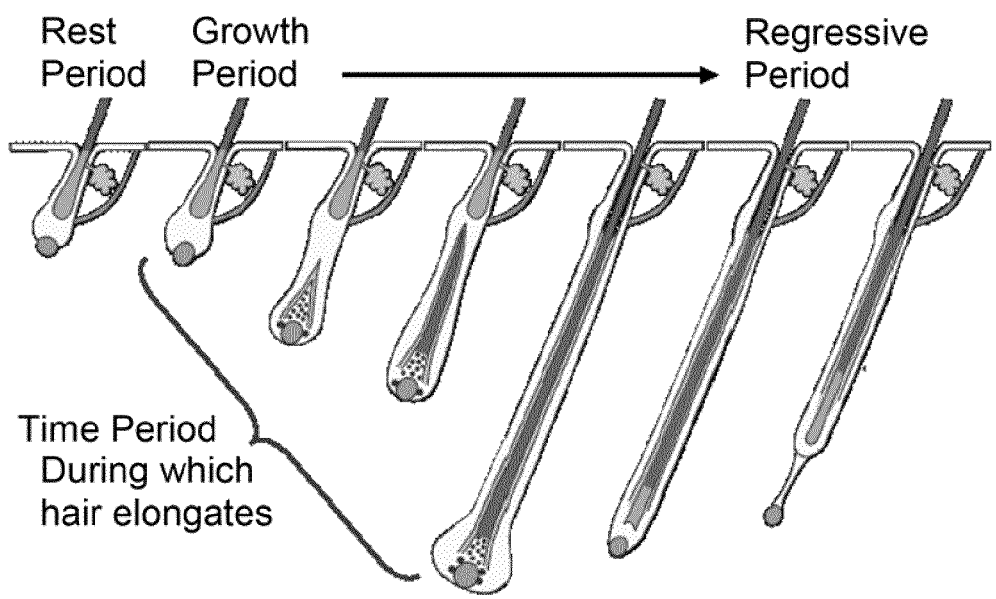
FIG. 8 is an explanatory drawing of the hair cycle.

In other words, although hair (body hair) is known to have a hair cycle in which hair changes from a growth period to a regressive period and then to a rest period (see FIG. 8), as a result of repeated irradiation of light as described above, a hair cycle results in which the growth period has shortened, thereby making it possible to transform hair growth to a state in which hairs on the skin surface are narrow and do not grow that much. Furthermore, since this type of change in the hair cycle is merely a change in the cycle pattern while the series of tissue changes that accompany the hair cycle are normal for the body, there are no detrimental effects on the human body.

Figure 9:
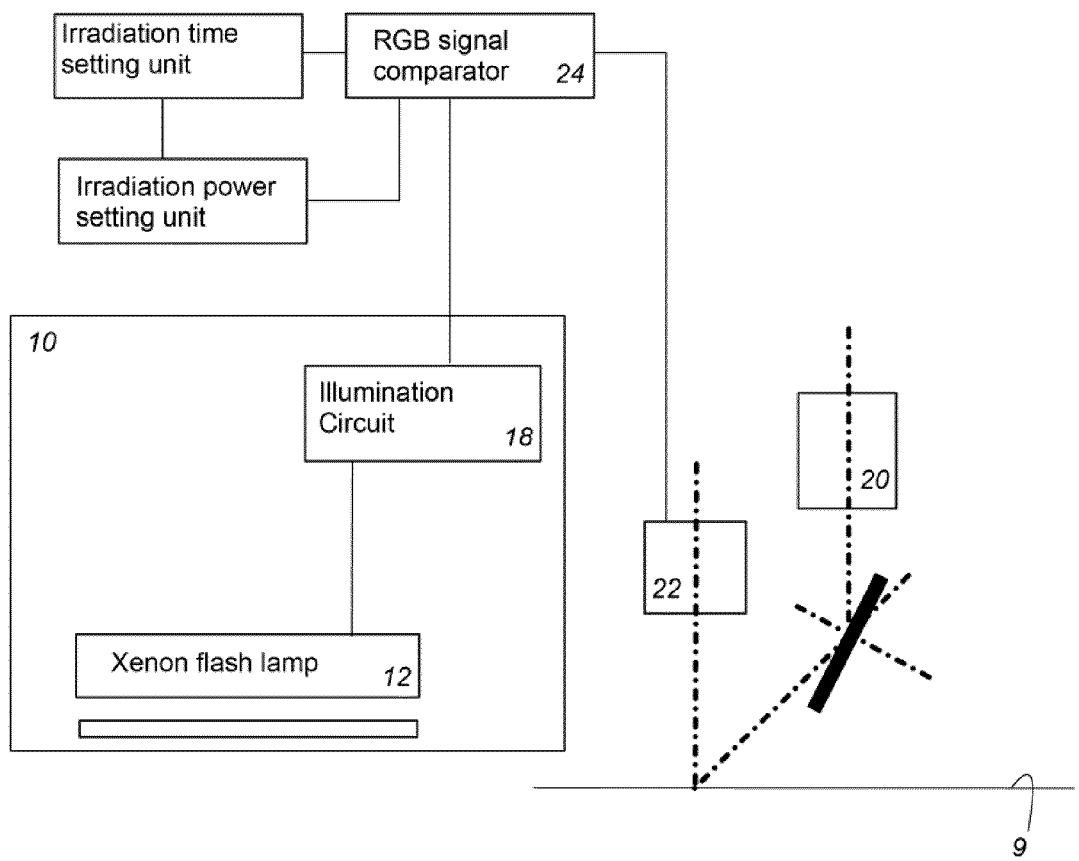
FIG. 9 is a block diagram showing a hair growth modulation device in the present invention.

FIG. 9 shows a hair growth modulation device provided with a function that controls irradiation of modulating light to a target site. In addition to a modulating light irradiator 10 that uses a xenon flash lamp for the light source 12, this device is provided with a irradiation time setting unit 26 that sets the irradiation time of modulating light, an irradiation power setting unit 28 that sets the irradiation power of modulating light, a white LED 20 for projecting light for measuring skin reflection properties, a light receiver 22 that receives diffused reflected light from a direction inclined at 45° with respect to incident direction on the skin when projecting light onto skin 9 via a mirror 27, and an RGB signal comparator 24 that processes RGB signals of various brightness obtained from the light receiver 22 having respective RGB color filters. Furthermore, a sophisticated analyzer such as a spectral reflectance measuring device may be used instead of the RGB color filters.

The comparator 24 is cooperative with the irradiation time setting unit 26 and the irradiation power setting unit 28 to judge whether or not the light source 10 irradiates the skin with the light on the basis of the brightness signals, and to determine the irradiation time S and irradiation power P of the light source 10 when the light source 10 irradiates the skin with the light. Here, an illumination circuit 18 causes the xenon flash lamp 12 to emit the light, so that the xenon flash lamp 12 irradiates the skin with the modulating light through the band pass filter 14.

Figure 10:
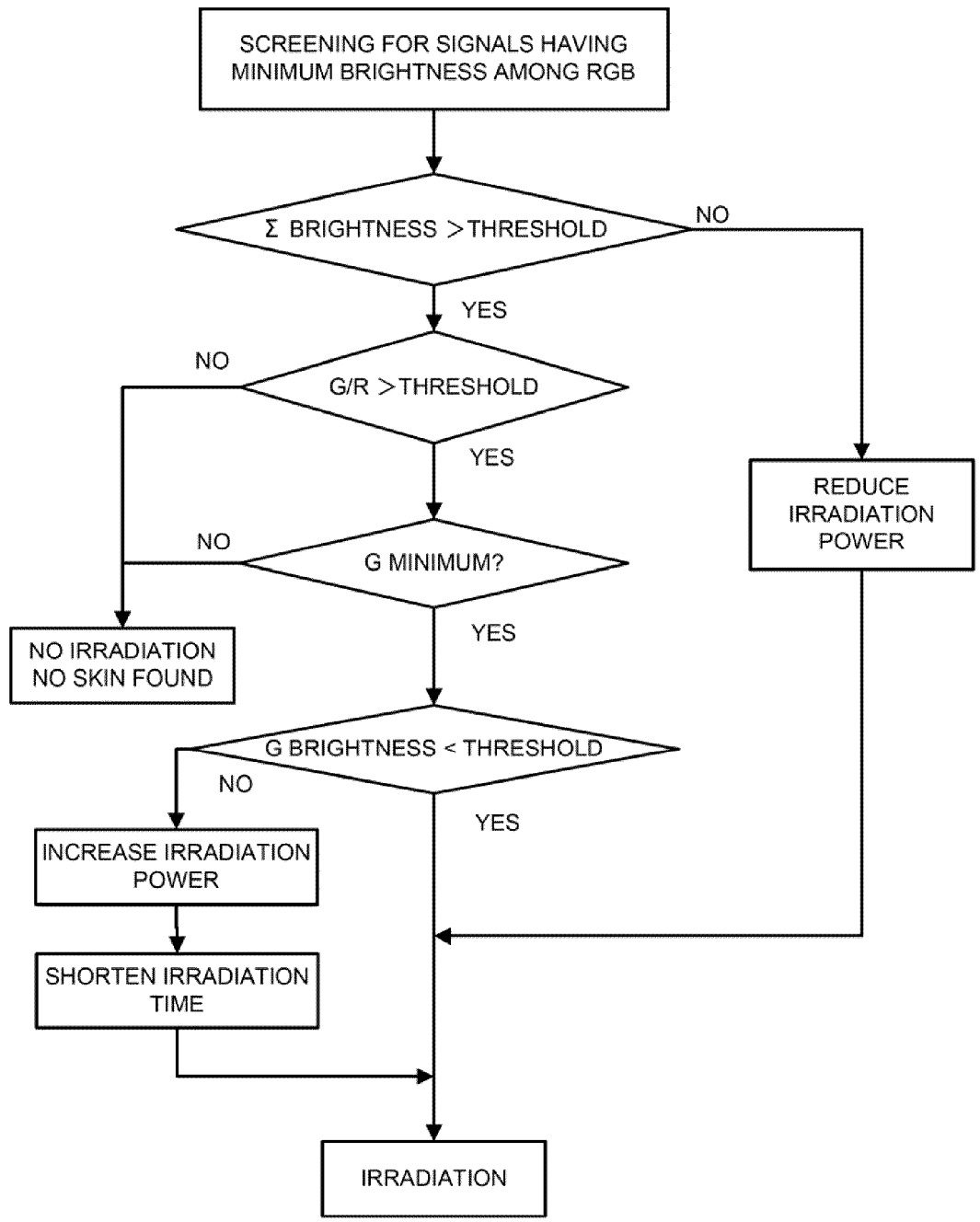
FIG. 10 is a flow chart that explains operation of the device in the present invention.

The flow chart of FIG. 10 indicates operation regarding the judgment of whether or not irradiation of modulating light is to be allowed and determination of irradiation conditions in the device described above. In the case the sum E of each brightness among the received RGB signals is lower than a preset threshold value, the skin can be judged to have become dark due to sun tanning resulting in a decrease in reflectance. In skin that has become dark due to sun tanning, melanin levels are high and extend throughout the skin. Since this results in a state in which light is easily absorbed, irradiation power P is decreased.

Next, the brightness ratio between R and G is examined. Although the G/R ratio normally has a somewhat large value in the case of skin that is not sun tanned, in the case of skin that has become red due to sun tanning, the value of the G/R ratio decreases. If the value of the G/R ratio is smaller than a prescribed threshold value, the skin at the target site is judged to exhibit redness due to sun tanning, and since inflammation is occurring within the skin, irradiation of modulating light is prohibited.

Moreover, in the case of comparing each of the R, G and B brightness signals and the brightness of G is not at a minimum, the target site is judged to be a site other than the skin that should not be irradiated such as an eyeball, and that site is not irradiated.

Figure 11:
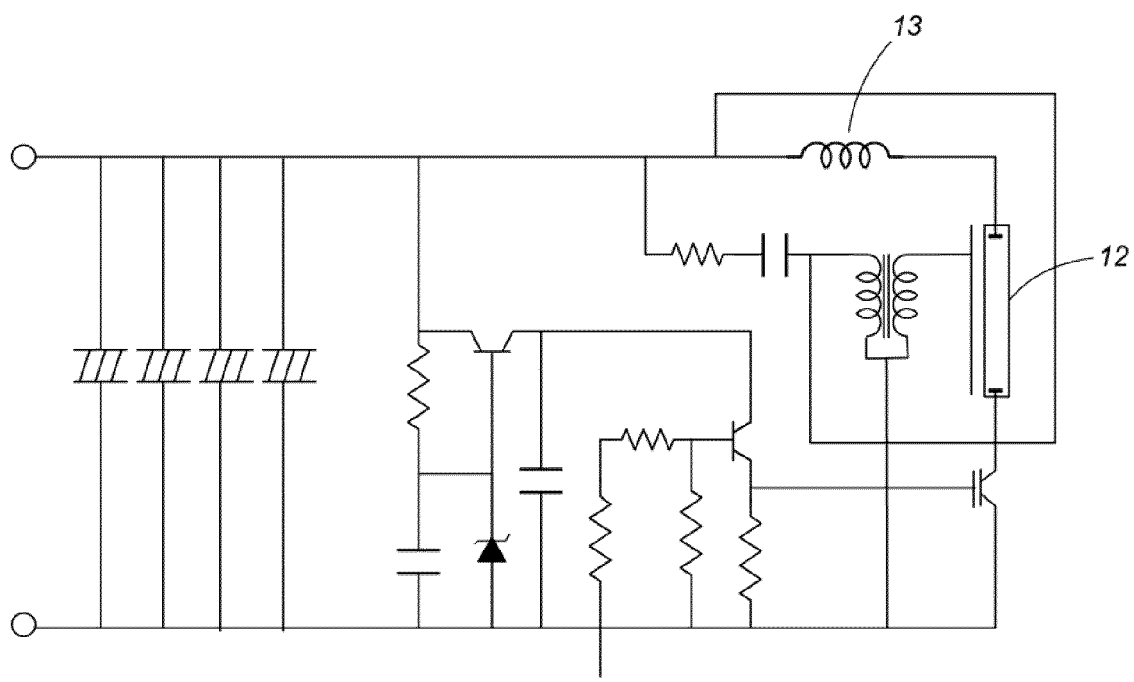
FIG. 11 is a circuit diagram of an illumination circuit used in the device in the present invention.

Although irradiation is carried out after going through these steps to confirm safety, at this time, in the case the irradiation power P is larger than a threshold value preset for the brightness of G, the power is increased to enhance effects and irradiation time is shortened accompanying that increase. More specifically, in the illumination circuit shown in FIG. 11, the value of an inductor 13 that controls irradiation time is changed, and this causes a change in capacity of the capacitor.

Hair growth in the growth period of the hair cycle has been confirmed in mice and humans to conversely proceed rapidly if light is irradiated during the rest period of the hair cycle. On the basis thereof, irradiation of light as described above not only inhibits hair growth but also has an effect with respect to hair growth and hair regeneration. Since the durations of the growth period, regressive period and rest period of the hair cycle vary according to the location such as the arms or scalp, light is irradiated after determining whether the hair cycle is in the rest period or the growth period depending on whether hair growth is desired to be promoted or inhibited at the irradiated location.

The invention claimed is:

1. A hair growth modulating method comprising a step of irradiating a modulating light having a wavelength of 400 nm to 600 nm at an energy of 0.01 J/cm$^2$ to 1 J/cm$^2$ to a portion around hair roots of a human such that the modulating light is absorbed by a light absorptive component of the human body existing around the hair roots,
   wherein the modulating light is irradiated at illuminance of 1,500,000 to 7,000,000 lux.

2. A hair growth modulating method as set forth in claim 1, wherein
   said modulating light is selected to have a wavelength excluding a range of 900 nm to 1500 nm.

3. A hair growth modulating method as set forth in claim 1, wherein
   said modulating light is irradiated over a time period of not more than millisecond.

4. A hair growth modulation device comprising a light irradiator configured to irradiate said modulating light as defined in claim 1.

5. A hair growth modulation device comprising
   a light irradiator configured to irradiate a modulating light having a wavelength distribution of 400 nm to 600 nm to a human body;
   a measurement means configured to measure an absorption spectrum that the human body absorbs upon being irradiated with said modulating light;
   a control means configured to compare a peak value of absorption rate at said absorption spectrum measured by said measurement means with an absorption rate at a specific wavelength for variably regulating a power of said modulating light and an irradiation time period,
   wherein the modulating light is irradiated at illuminance of 1,500,000 to 7,000,000 lux.

6. A hair growth modulation device as set forth in claim 5, wherein
   said control means is configured to control the power and the irradiation time for irradiating the light beam at a constant energy.

7. A hair growth modulating method as set forth in claim 2, wherein
   said modulating light is irradiated over a time period of not more than 1 millisecond.

8. A hair growth modulation device comprising a light irradiator configured to irradiate said modulating light as defined in claim 2.

9. A hair growth modulation device comprising a light irradiator configured to irradiate said modulating light as defined in claim 3.

10. A hair growth modulation device comprising a light irradiator configured to irradiate said modulating light as defined in claim 7.

* * * * *